(12) United States Patent
Jonkers et al.

(10) Patent No.: US 10,093,579 B2
(45) Date of Patent: Oct. 9, 2018

(54) PROCESS FOR THE PRODUCTION OF CEMENTITIOUS MATERIAL

(71) Applicant: TECHNISCHE UNIVERSITEIT DELFT, Delft (NL)

(72) Inventors: Hendrik Marius Jonkers, Delft (NL); Reneé Maria Mors, Delft (NL)

(73) Assignee: GREEN-BASILISK B.V., Delft (NL)

( * ) Notice: Subject to any disclaimer, the term of this patent is extended or adjusted under 35 U.S.C. 154(b) by 36 days.

(21) Appl. No.: 15/325,207

(22) PCT Filed: Jul. 17, 2015

(86) PCT No.: PCT/NL2015/050526
§ 371 (c)(1),
(2) Date: Jan. 10, 2017

(87) PCT Pub. No.: WO2016/010434
PCT Pub. Date: Jan. 21, 2016

(65) Prior Publication Data
US 2017/0190620 A1    Jul. 6, 2017

(30) Foreign Application Priority Data
Jul. 17, 2014  (NL) .................................. 2013203

(51) Int. Cl.
| C04B 16/06 | (2006.01) |
| C04B 18/08 | (2006.01) |
| C04B 18/14 | (2006.01) |
| C04B 28/02 | (2006.01) |
| C04B 103/00 | (2006.01) |
| C12N 1/20 | (2006.01) |
| C04B 14/28 | (2006.01) |
| C04B 14/06 | (2006.01) |

(52) U.S. Cl.
CPC .............. *C04B 28/02* (2013.01); *C04B 14/06* (2013.01); *C04B 14/28* (2013.01); *C04B 16/0625* (2013.01); *C04B 16/0633* (2013.01); *C04B 16/0641* (2013.01); *C04B 16/0683* (2013.01); *C04B 16/0691* (2013.01); *C04B 18/08* (2013.01); *C04B 18/141* (2013.01); *C12N 1/20* (2013.01); *C04B 2103/0001* (2013.01)

(58) Field of Classification Search
CPC .... A61K 6/0017; A61K 6/0038; A61K 6/083; A61K 6/087; A61K 6/097; A61K 6/0067; A61K 6/0612; C08L 1/284; C08L 23/20; C08L 71/02; C08L 7/00; C08L 91/005; A01N 25/10; A01N 25/30; A61L 2300/406; A61L 2300/44
See application file for complete search history.

(56) References Cited

U.S. PATENT DOCUMENTS 8,911,549 B2 * 12/2014 Jonkers ............... C04B 20/1022
                                                106/499
2013/0112114 A1 * 5/2013 Jonkers ............... C04B 20/1022
                                                106/661

FOREIGN PATENT DOCUMENTS

WO    WO 2011/126361    10/2011

OTHER PUBLICATIONS

International Search Report for PCT/NL2015/050526, dated Oct. 14, 2015, 4 pages.
Written Opinion of the ISA for PCT/NL2015/050526, dated Nov. 14, 2016, 24 pages.
International Preliminary Report on Patentability for PCT/NL2015/050526, dated Oct. 14, 2015, 4 pages.
Jonkers "Bacteria-based self-healing concrete", Delft University of Technology, Heron, vol. 56 (2011), No. 1/2, Jan. 31, 2011, 12 pages.
Jonkers et al., "Crack repair by concrete-immobilised bacteria", Delft University of Technology, Heron, vol. 56 (2011), No. 1/2, 31 Jan. 31, 2007, 8 pages.
Wiktor et al., "Development of a liquid bio-based repair system for aged concrete structures", Concrete Repair, Rahabilitation and Retrofitting III, XP 002718949, 2012, pp. 955-960.

* cited by examiner

*Primary Examiner* — Debbie K Ware
(74) *Attorney, Agent, or Firm* — Nixon & Vanderhye P.C.

(57) ABSTRACT

The invention provides a process for the production of a cementitious material, comprising mixing cement starting materials, a healing agent and a fibrous reinforcing material, wherein the healing agent comprises bacterial material, and wherein the fibrous reinforcing material comprises a biodegradable polymer, having an average molecular weight selected from the range of 10-1500 kg/mol, and wherein the fibrous material comprises fibers having diameters selected from the range of 5-750 μm, and having lengths selected from the range of 50 μm-150 mm.

17 Claims, No Drawings

PROCESS FOR THE PRODUCTION OF CEMENTITIOUS MATERIAL

This application is the U.S. national phase of International Application No. PCT/NL2015/050526 filed 17 Jul. 2015, which designated the U.S. and claims priority to NL Patent Application No. 2013203 filed 17 Jul. 2014, the entire contents of each of which are hereby incorporated by reference.

FIELD OF THE INVENTION

The invention relates to a process for the production of cementitious material as well as to a (hardened) construction element based on such cementitious material. The invention also relates to a method for the production of such construction element.

BACKGROUND OF THE INVENTION

Autogenously crack-healing of concrete has been recognized in the art. Mainly micro-cracks with widths typically in the range of 0.05 to 0.1 mm have been observed to become completely sealed particularly under repetitive dry/wet cycles. The mechanism of this autogenously healing is mainly due to secondary hydration of non- or partially reacted cement particles present in the concrete matrix. Due to capillary forces water is repeatedly drawn into micro cracks under changing wet and dry cycles, resulting in expansion of hydrated cement particles due to the formation of calcium silicate hydrates and calcium hydroxide (Portlandite). These reaction products are able to completely seal cracks provided that crack widths are small. Larger sized cracks can only be partially filled due to the usually limited amount of non-reacted cement particles present. In the latter case healing activity is insufficient as it results only in the formation of a thin layer of hydration products on the crack surface. Besides secondary hydration, also the process of carbonation can contribute to the crack-sealing capacity of commonly applied concrete. This reaction is also expansive, as ingress atmospheric carbon dioxide ($CO_2$) reacts with calcium hydroxide (Portlandite) particles present in the concrete matrix to yield various calcium carbonate minerals such as calcite, aragonite and vaterite.

From a durability perspective, rapid sealing of particularly freshly formed surface cracks is important as this process can substantially delay the ingress of water and other aggressive chemicals into the concrete matrix and thus prevent early material degradation. Several chemicals such as sulphate, chloride and acids are known to dramatically increase concrete matrix degradation and corrosion of embedded steel reinforcement causing a serious threat to the materials performance and durability. One possibility to improve the self-healing capacity of cementitious materials is by decreasing the water/cement ratio of the original mixture. A substantial increase in the relative amount of cement or binder in the mixture results in formation of a self-healing buffer, i.e. the presence of a significant amount of non- or only partially reacted binder particles present in the material matrix. Typical examples of such low water to binder ratio types of concrete are high strength or high performance concretes. As recent studies have shown, such concretes do indeed possess a superior crack-sealing capacity compared to ordinary concretes characterized by higher water to cement ratios.

However, from an environmental viewpoint the latter concrete types (i.e. ordinary types) are preferred as less cement per concrete volume is used. The lower the amount of cement in concrete the lower the environmental pressure in terms of atmospheric $CO_2$ emissions. Although high strength concrete allows building of more slender structures than ordinary concrete and thus need less concrete volume, the total amount of cement used is still significantly higher due to the inherent high percentage of non- or partially hydrated cement particles in the material matrix. The development of a self-healing mechanism in concrete that is based on a potentially cheaper and more sustainable material than cement could thus be beneficial for both economy and environment.

Although bacteria, and particularly acid-producing bacteria, have been traditionally considered as harmful organisms for concrete, recent research has shown that specific species such as ureolytic and other types of calcite-producing bacteria can actually be useful as a tool to repair surface cracks in concrete. In some studies bacteria were externally and manually applied on the concrete surface. Species from the *Bacillus* group appear promising intrinsic agents as their spores, specialized thick-walled dormant cells, have been shown to be viable for over 200 years under dry conditions. Such bacteria would comprise one of the two components for the envisioned autogenous healing system.

For crack repair filler material is needed, and bacteria can produce that by metabolic conversion of a suitable organic component. The nature of metabolically produced filler material could be bio-minerals such as calcite. These calcium carbonate based minerals are relatively dense and can block cracks, and thus hamper ingress of water efficiently, as was previously demonstrated. One particular challenge in the development of self healing materials is the need to incorporate sufficient healing agent in the material matrix. As the healing capacity, i.e. the volume of cracks that can potentially be filled may directly be related to the amount of precursor material present, a substantial volume of the material needs to be reserved in order to obtain a significant healing potential. While the matrix-incorporated bacteria function as catalyst and therefore need only a limited volume, it is typically the mineral precursor compound, the second component of the healing system, which will occupy a substantial volume when a significant healing capacity is needed. Particularly for larger cracks to become completely sealed, bulky internal reservoirs or alternatively an intrinsic transportation mechanism is needed. In concrete the latter could be provided by the water-filled continuous capillary pore system which is usually present. The mineral precursor compound could be present in dissolved state in the matrix pore water without affecting strength properties of the material what presumably occurs when specific internal healing agent containing reservoirs are needed. In any case however, incorporated bacteria and the mineral precursor compound should compromise concrete strength properties only to an acceptable extend.

EP2082999 describes a healing agent in cement-based materials and structures, wherein said healing agent comprises organic compounds and/or bacteria-loaded porous particles, which porous particles comprise expanded clay- or sintered fly ash. Furthermore, said porous particles are intact spheres, broken or crushed particles derived from said intact spheres, having a specific density between 0.4 and 2 g cm$^{-3}$.

SUMMARY OF THE INVENTION

Prior art cementitious materials suffer from crack formation. Hence, it is an aspect of the invention to provide an alternative process of making a cementitious material and/or an alternative construction element (from such cementitious material) which preferably does not suffer from crack formation and/or which self heals cracks.

A possibility to maintain strength and/or other desired properties (such as liquid impermeability) is to add bacteria to the cementitious material, such as in the form of a healing agent, which bacteria may repair smaller cracks. Hence, it is an aspect of the invention to provide bacterial material to the starting material of the cementitious material. It further surprisingly appears that when adding biodegradable polymeric material, this biodegradable material may be used by the bacteria as substrate. By adding biodegradable fibrous reinforcement, for instance as individual fibers (herein also indicated as fiber particles) or as a textile (e.g. yarn, fabric), it surprisingly may seem that the fibers in the first stage of hardening assist in getting a strong cementitious material; after formation or setting of the cementitious material, such as within a few weeks from making the cementitious material and starting to harden it, it appears that the fibers can be degraded without substantial loss of strength and/or other desired properties. As crack formation is a process that occurs over time, the biodegradable polymeric material may be consumed by the bacteria for crack reparation. Hence, advantageously, the biodegradable polymer in the form of fibers assists first in hardening and then also in maintenance of the cementitious material. Hence, in an embodiment, the fibres are provided as textile of fibres. In yet another embodiment, the fibres are provided as fibre particles (having the herein indicated dimensions). A textile of fibres may e.g. refer to a yarn or a fabric. The textile may be woven or non woven. Herein, the term "textile" especially refers to an aggregate or woven unit comprising a plurality of individual fibers (which individual fibers have (average) diameters selected from the range of 5-750 µm, and having (average) lengths selected from the range of 50 µm-150 mm). In an embodiment, the textile is provided as textile patch.

Hence, in a first aspect the invention provides a process for the production of a cementitious material, comprising mixing cement starting materials, a healing agent and a fibrous reinforcing material, wherein the healing agent comprises bacterial material, and wherein the fibrous reinforcing material comprises a biodegradable polymer, especially having an average molecular weight selected from the range of 10-1500 kg/mol, and wherein the fibrous material especially comprises fibers having (average) diameters selected from the range of 5-750 µm, and having (average) lengths selected from the range of 50 µm-150 mm.

In yet a further aspect, the invention also provides a cementitious material comprising (a) cement, (b) one of more of slag, ash, limestone and sand, (c) optionally super plasticizer, (d) healing agent, and (e) fibrous reinforcing material, wherein the healing agent comprises bacterial material, wherein the fibrous reinforcing material comprises a biodegradable polymer, having an average molecular weight selected from the range of 10-1500 kg/mol, and wherein the fibrous material comprises fibers having diameters selected from the range of 5-750 µm, and having lengths selected from the range of 50 µm-150 mm, having a weight ratio of healing agent to (a) cement, and (b) one of more of slag, ash, limestone and sand selected from the range of 0.2:100-10:100, and/or having a weight ratio of fibrous reinforcing material to (a) cement, and (b) one of more of slag, ash, limestone and sand selected from the range of 0.1:100-10:100. Further, the invention especially provides a cementitious material obtainable by the process as described herein.

In another aspect, the invention provides a method for the production of a construction element, the method comprising providing the cementitious material as defined herein, and allowing the cementitious material to harden at a predetermined place or in a predetermined mold.

Further, the invention provides a construction element comprising hardened cementitious material, wherein the cementitious material further comprises bacterial material and one or more of (i) fibrous reinforcing material comprising a biodegradable polymer, and (ii) a conversion product of a bacterial conversion of the fibrous reinforcing material comprises a biodegradable polymer.

The invention uses degradable fibrous polymer which features a double functionality in cementitious materials, such as mortar and concrete. In a further embodiment, the invention uses fibrous reinforcing material comprising a biodegradable polymer featuring a double function. The first functionality provides a contribution to structural integrity, which is obtained via reinforcement, serving crack width control in early age restrained shrinkage situations. The second functionality is provided by polymer degradation over time, by which the degradation product can serve as a precursor compound for bacterial metabolic conversion into crack sealing material. In this way functionality can be regained, such as liquid tightness. Stresses cause delamination or cracking. Incorporation of fibrous reinforcement creates multiple cracks of limited widths, which are easier to close. Significant advantage is that the proposed degradable fibrous reinforcing material serves a dual function, enabling optimum use of properties. In the early age it is used structurally, as current fibers. After serving its structural purpose the material becomes available for a second functional purpose, namely as a compound for bacterial conversion. In the process minerals are deposited on the crack wall, preventing ingress of water or deleterious substances.

The invention solves two issues by one method, resulting in lower costs and a reduction in maintenance and repair during the service life of the cementitious element. An additional benefit is the biological base of the proposed degradable fibrous reinforcement, since currently common used materials are synthetic and therefore less sustainable. Since the invention combines two functions without modifying the system and offers a biological alternative, the material may directly replace a part of the fibrous reinforcement currently in use. The proposed degradable fibrous reinforcement can be applied to cementitious repair products. Furthermore it can (partially) replace crack width limiting reinforcement, currently made of steel.

DETAILED DESCRIPTION OF THE EMBODIMENTS

A suitable biodegradable polymer may include one or more of polyglycolide, polylactide, polyhydroxybutyrate, chitosan, hyaluronic acid, and a hydrogel. Another suitable biodegradable polymer may include one or more of poly(2-hydroxyethyl-methacrylate) and poly(ethylene glycol). In general, most aliphatic polyesters are biodegradable due to their potentially hydrolysable ester bonds. Hence, a suitable biodegradable polymer may also include one or more a polyhydroxyalkanoate (PHA) (like the poly-3-hydroxybutyrate (PHB)), a polyhydroxyvalerate (PHV), a poly-hydroxyhexanoate (PHH), polylactic acid (PLA), polybutylene succinate (PBS), poly-caprolactone (PCL), a polyanhydride, a polyvinyl alcohol, starch or a starch derivative, cellulose or a cellulose ester (like cellulose acetate and nitrocellulose) and a cellulose derivative (celluloid), protein or cellulose derived polymers from sea weed, wood, soy bean and milk, etc. In a specific embodiment, the biodegradable polymer is selected from the group consisting of polybutylene succinate (PBS), polyhydroxybutyrate (PHB), and poly lactic acid (PLA). In another embodiment, the fiber is selected from the group of alternative fibers for natural wool, such as one or more of a natural seaweed cellulose-based fiber (such as SeaCell™), a soybean protein fiber ("Soy Silk"), a wood cellulose fiber (such as Tencel®), and a milk protein fiber ("Milk Wool"). In yet another specific embodiment, the biodegradable polymer is selected from the group consisting of polysaccharides, such as one or more of alginate, chitin and chitosan. Especially, the biodegradable polymer may comprise an alginate. The biodegradable material may degrade per se, e.g. amongst others under the influence of alkaline conditions, and/or may also be degraded by the bacteria. The biodegradable polymer, especially its degradation products (such as monomers like lactate, succinate, hydroxybutyrate, etc.) may be used by the bacteria as substrate to grow the structures in cracks. Hence, the biodegradable polymer is especially biodegradable under alkaline conditions.

Of course, a combination of two or more different biodegradable polymers may be applied. Further, the biodegradable polymers in general have a weight distribution. As indicated above, the biodegradable polymer especially has a (weight) average molecular weight selected from the range of 10-1500 kg/mol (i.e. 10-1500 kDa), even more especially in the range of 100-1000 kg/mol (i.e. 100-1000 kDa). Lower average molecular weights may lead to a too fast degrading product not providing enough strength whereas too high average molecular weights may lead to fibers that have a too slow degradation. Further, the fibrous material may be reinforced, e.g. with a clay, a zeolite, a montmorillonite, flax, etc. Especially, the fibrous reinforcing material may comprise at least 10 wt. %, such as at least 20 wt. %, such as at least 40 wt. %, such as 50-100 wt. % biodegradable polymer. In an embodiment, the fibrous reinforcing material comprises biodegradable fibers. In a further embodiment, the fibrous reinforcing material comprises a biodegradable coating. Especially, in an embodiment the fibrous reinforcing material comprises 100% biodegradable polymer. Hence, in an embodiment the fibers may comprise non-biodegradable material and biodegradable polymers, such as fibers with a coating of the latter, and in another embodiment the fibers essentially consist of biodegradable polymers. In the latter embodiment, the fibers may be consumed by the bacteria entirely.

Further, as indicated above, the fibrous material especially comprises fibers having (average) diameters selected from the range of 5-750 μm, and having (average) lengths selected from the range of 50 μm-150 mm. The fibers do not need to have mono disperse size distribution. The sizes may have a (broad) distribution. However, especially the (number) averaged sizes comply with the herein indicated dimensions. In a specific embodiment, wherein the fibrous material comprises fibers having (average) diameters selected from the range of 10-100 μm, and having (average) lengths selected from the range of 0.5 mm-150 mm. Larger sizes then herein indicated may lead to complications during the production process and/or hardening process, and/or may lead to a too slow degradation. Too small sizes may lead to a too low impact on initial hardening and/or a too fast degradation. In an embodiment, the aspect ratio (length of the fibre/diameter of the fiber) is selected from the range of 30-250.

In yet a further specific embodiment, the fibrous material comprises fibers having (average) lengths selected from the range of 50 μm-500 μm. Such micro fibers may especially be advantageous for cementitious mixtures featuring fine filler material (≤125 μm), such as cement pastes. For mortar featuring aggregates ≤4 mm (including also e.g. sand), however, fibers have typical (average) lengths selected from the range of 0.5-20 mm. For concrete featuring aggregates >4 mm (including also e.g. gravel), fibers have typical (average) lengths selected from the range of 15-150 mm. Especially the size of the fiber is at least equal to the size of the largest aggregate (particle(s)). Especially the fibers have a length selected from the range of 1-100, especially 2-10 times the (typical) size of the largest (type of) aggregate (such as the (typical) size of the largest sand particles, or the (typical) size of the largest gravel particles, or the (typical) size of the largest healing agent elements, etc., whichever compound of the cementitious mixture has the largest size).

The aggregates (and the different compounds) may not have a mono-disperse size distribution. The sizes may have a (broad) distribution. The typical size of the largest aggregate, especially does not have to be the size of the absolute largest aggregate. The typical size especially is determined by the size of the aggregates that are part of the 10%—by weight—largest aggregates). Especially the length of the fiber is selected to be larger than the weight averaged size of the largest 10% (by weight) of the aggregates in the cementitious mixture, such as 2-30 time larger than the weight averaged size of the largest 10% (by weight) of the aggregates in the cementitious mixture.

The weight ratio of the fibrous reinforcing material to the starting dry materials (see also below), especially to the cement and one or more of the slag, ash, limestone and sand is selected from the range of 0.1:100-10:100 (0.1%-10%).

In an embodiment, the fibers are especially not coated or are coated with a degradable or dispersible coating. Especially, under the (alkaline) conditions such coating has a sacrificial character, such as featuring (substantially) higher degradation than the biodegradable polymer fiber. In yet another embodiment, the fibers may be coated by a biodegradable polymer, especially wherein the fiber may be selected from the range of substantially completely biodegradable to substantially completely not biodegradable. Especially the fiber may (also) be (entirely) biodegradable.

Hence, the invention also provides a process for the production of a cementitious material, comprising mixing cement starting materials, a healing agent and a fibrous reinforcing material, wherein the healing agent comprises bacterial material, and wherein the fibrous reinforcing material comprises a biodegradable polymer, which is especially biodegradable under alkaline conditions, and wherein the biodegradable polymer has an (weight) average molecular weight in the range of 100,000-1,000,000 g/mol.

During the lifetime of the hardened cementitious material, even during the hardening process, cracks may be formed. This leads to cavities in the element. Herein the term "cavity" especially relates to "crack". For instance, crack formation caused by dynamic and static stress on concrete structure elements is due to working loads and permanent load. Thermal and chemical impacts and frost de-icing stress in the pore system of the concrete are also important. Permanent weathering, horizontal surfaces, dark surfaces and sharp edges increase the risk of crack formation and/or flaking due to increased thermal strain and unfavorable stresses in the building component. Cracks may for instance have dimensions such as by way of example 0.1 cm-1 m length and 0.01-10 mm width, though other dimensions may also be possible. However, the term cavity may also relate to pore. Pores have in general dimensions like length, width and depth in the range of 0.1-5 mm.

The healing agent may (also) comprise one or more of a silicate source, such as (sodium) silicate, a calcium source, such as calcium nitrate, and a nutrient for bacteria. The calcium source is applied to build a new structure in the cavity, i.e. repair a crack. The calcium source may be used e.g. to form a phosphate and/or a carbonate. Especially, the calcium source may be used to form one or more of a phosphate and carbonate in an alkaline medium. This new structure is built with the bacteria. Hence, especially the bacterium is selected from the group consisting of bacteria that can form a phosphate or a carbonate precipitate in an alkaline medium. Due to the presence of the (sodium) silicate (or other material), the structure(s) that are built—by the bacteria—in the cavity may also comprise silicates (or other material). As bacteria are used to repair the cracks (by building e.g. calcium structures, such as calcium carbonate and/or calcium phosphate), the process is herein indicated as "bio-based reparation". The calcium source may especially comprise a calcium salt, such as calcium nitrate. Further, the healing agent may also comprise a phosphate source, such as a yeast extract or phytate or other biodegradable phosphate-containing organic compound.

To obtain the new (calcium) structures in the cavities, the healing agent may at least include building material, bacteria, and a nutrient for the bacteria. As indicated above, the building material at least comprises calcium from a calcium source. The combination of building material, bacteria, and nutrient for the bacteria may herein also be indicated as "healing agent", or "bio-based healing agent". The healing agent, when incorporated in concrete, may perform autonomous repair of cracks formed in the material when activated by water. The healing agent comprises the bacterial material and preferably also an additive (such as the nutrient).

The bacteria are especially provided in dried (powder) form and can especially be either lyophilized vegetative cells or dried bacterial spores. Hence, the bacterial material is selected from the group consisting of a bacterium, a lyophilized bacterium and a bacterial spore of a bacterium. In the liquid, the bacterial material is especially selected from the group consisting of a bacterium and a bacterial spore of a bacterium.

The term "bacterial material" may also refer to a combination of bacterial materials, such as a combination of two or more of the bacterium, the lyophilized bacterium and the bacterial spore of a bacterium. The term "bacterial material" may alternatively or additionally also refer to a combination of different types of bacteria, such as two or more of *Planococcus, Bacillus* and *Sporosarcina*, or such as a combination of an anaerobic bacterium and an aerobic bacterium.

Hence, in an embodiment, the bacterium is selected from the group consisting of bacteria that can form a phosphate or a carbonate precipitate in an alkaline medium (such as calcium carbonate or a calcium phosphate based mineral, like apatite). In an embodiment, the bacterium is selected from the group consisting of aerobic bacteria. An advantage of using aerobic bacteria may be that healing agents comprising bacterial material of aerobic bacteria may be used in application wherein the hardened cementitious material is exposed to aerobic conditions. In another embodiment, the bacterium is selected from the group consisting of anaerobic bacteria. An advantage of using anaerobic bacteria may be that healing agents comprising bacterial material of anaerobic bacteria may be used in application wherein the hardened cementitious material is exposed to anaerobic conditions, such as underground applications. Preferred bacteria are selected from the group of (facultative aerobic bacteria from genera such as) *Planococcus, Bacillus* and *Sporosarcina*, especially *Bacillus*. Especially bacteria are selected which can grow by anaerobic fermentation and/or anaerobic nitrate reduction. Examples of (other) enzymes that can be used include one or more of a protease, an esterase, a glycosidase, and a manganese peroxidase, etc.

Hence, in summary the bacterium may be selected from the group consisting of aerobic bacteria or the bacterium is selected from the group consisting of anaerobic bacteria; combinations may also be used. Further, the bacterium may be selected from the group of genera consisting of *Planococcus, Bacillus* and *Sporosarcina*. Also, the bacterium may be selected from the group of denitrifying bacteria. Combinations may also be used.

Further, in addition to the bacterial material, the healing agent may comprise a nutrient and a calcium source. The healing agent may comprise one or more organic and/or calcium-containing compounds which can be metabolically converted by active bacteria in an alkaline environment to bio-minerals such as calcium carbonate or calcium phosphate. The organic and/or calcium-containing compounds may produce, after metabolic conversion by bacteria (in an alkaline environment), phosphate and/or carbonate ions, and calcium ions, which form substantially water insoluble precipitates such as calcium carbonate based minerals (like calcite, aragonite, vaterite) and/or calcium phosphate based minerals (e.g. apatite). Examples of organic and/or calcium-containing compounds are organic calcium salts, such as calcium formate, calcium acetate, calcium lactate, calcium gluconate, calcium nitrate, a carbohydrate, a fatty acid, a amino acid, a lactate, a maleate, a formate, a sugar, a pyruvate and an organic phosphate containing compounds, such as a phytate. The calcium-based precursors are herein also indicated as "biomineral precursor" or "calcium biomineral precursor".

In yet a further embodiment, the healing agent comprises a bacterial growth factor, such a selected from the group consisting of a yeast extract, a peptone, an aspartate, a glutamate and trace elements. Preferably, the bacterial growth factor comprises trace elements and one or more selected from the group consisting of a yeast extract, a peptone, an aspartate, and a glutamate. The trace element especially comprises one or more elements selected from the group comprising Zn, Co, Cu, Fe, Mn, Ni, B, P and Mo.

Especially, the healing agent may comprise one or more compounds selected from the group consisting of an organic compound, preferably selected from the group consisting of a yeast extract, a peptone, a carbohydrate, a fatty acid, an amino acid, a lactate, a glutamate, an aspartate, a glutamate, a maleate, a formate, a sugar and a pyruvate.

Therefore, in a preferred embodiment, the healing agent comprises (1) one or more compounds selected from the group consisting of calcium formate, calcium acetate, calcium lactate, calcium gluconate, calcium nitrate, a carbohydrate, a fatty acid, a amino acid, a lactate, a maleate, a formate, a sugar, a pyruvate and a phytate and (2) a bacterial growth factor, preferably selected from the group consisting of a yeast extract, a peptone, an aspartate, a glutamate and trace elements. Preferably, the additive comprises a calcium compound and an organic compound (such as, a carbohydrate, a fatty acid, a amino acid, a lactate, a maleate, a formate, a sugar, and a pyruvate), as well as trace elements and one or more of a yeast extract, a peptone, an aspartate, and a glutamate. Instead of or in addition to the organic compound, the additive may also comprise a phytate. In an especially preferred embodiment, the additive comprises (a) a calcium compound, (b) one or more of an organic compound and a phosphor compound (such as phytate), (c) trace elements and (d) one or more of a yeast extract, a peptone, an aspartate, and a glutamate. Especially, the healing agent comprises a calcium compound selected from the group comprising calcium formate, calcium acetate, calcium lactate, calcium nitrate, and calcium gluconate.

Hence, in a specific embodiment, the nutrient comprises one or more compounds selected from the group consisting of an organic compound, a phosphor compound, and a nitrate compound. Especially, the nutrient comprises a nitrate compound. Hence, in an embodiment the nutrient comprise a nitrate compound and one or more other compounds. The nitrate compound may e.g. be provided as calcium nitrate (see also below). Further, the nutrient comprises one or more of a lactate and a gluconate, alternative to nitrate or in addition to nitrate. Especially, the nutrient comprises a yeast extract. This may be necessary for the bacteria to produce the structure in the cavity.

Herein, the term "cementitious material" may refer to the mixture that can be used as cement, or the mixture that can be used as concrete, or the mixture that can be used as mortar, etc. Hence, the term "cementitious material" especially refers to the flowable mixture that can be used to make a construction or construction element, and includes concrete, paste, grout, mortar, plaster, etc. The cementitious material is a binder and is a substance that sets and hardens as the cement reacts and which can e.g. bind other materials together. For instance, the cementitious material may be used as mortar in masonry or as concrete (which is a combination of cement and an aggregate) to form a construction element. Hence, the cementitious material can also be used to make construction elements, such as an element to be used in a building (see also below). The cementitious material may in an embodiment be hydraulic and may in another embodiment be non-hydraulic.

Especially, the cement starting material may include portland cement and water. Further, the starting material may include aggregate, such as gravel and/or sand. The starting material may include CaO (lime) and silica ($SiO_2$). Further, the starting material may comprise one or more of alumina ($Al_2O_3$), iron oxide ($Fe_2O_3$) and magnesium oxide (MgO). Further, the starting material may comprise one or more of sodium oxide ($Na_2O$) and sulphur trioxide ($SO_3$). The starting material may comprise further binder material such as slag (e.g. ground granulated blast-furnace slag), (fly) ash and limestone. The starting material may further comprise a super plasticizer or high range water reducer. Especially, super plasticizers may be comprised to avoid particle segregation and to improve the flow characteristics such as in concrete applications. Hence, the term "binder" may refer to cement and one or more of slag, ash, and limestone (when available). The terms "slag" and "ash" may each independently refer to one or more different types of such materials. Examples of slag and ash are provided herein. Also different types of limestone(s) may be used.

However, other or additional components in the cement starting material may also be present.

Suitable healing agents are also defined in WO2011126361 and EP2082999, especially WO2011126361, which are herein incorporated by reference. Hence, especially the healing agent may comprise a particulate healing agent, especially for a cementitious material, wherein the healing agent comprises in an embodiment coated particles and wherein the particles comprise bacterial material and additive, wherein the bacterial material is selected from the group consisting of a bacterium, a lyophilized bacterium and a bacterial spore of a bacterium, wherein the bacterium is especially selected from the group of genera consisting of *Planococcus, Bacillus* and *Sporosarcina*, or other relevant bacteria, including combinations of two or more thereof, and wherein the additive comprises (1) one or more compounds selected from the group consisting of calcium formate, calcium acetate, calcium lactate, calcium gluconate, a carbohydrate, a fatty acid, an amino acid, a lactate, a maleate, a formate, a sugar, a pyruvate and a phytate and (2) a bacterial growth factor selected from the group consisting of a yeast extract, a peptone, an aspartate, a glutamate and trace elements. The required amount of healing agent may depend on the expected number and size of cracks or cavities to be repaired. The amount of healing agent may further depend on the healing agent used (size, composition, etc.) Especially, the weight of the healing agent is at least 2% of the total weight of the cement and one or more of slag, ash, limestone and sand. Especially, the weight of the healing agent is comprises at maximum 10% of the total weight of the cement and one or more of slag, ash, limestone and sand.

The invention further provides a cementitious material comprising (a) cement, (b) one of more of slag, ash, limestone and sand, (c) optionally super plasticizer, (d) healing agent, and (e) fibrous reinforcing material, wherein the healing agent comprises bacterial material, wherein the fibrous reinforcing material comprises a biodegradable polymer, having an average molecular weight selected from the range of 10-1500 kg/mol. Further, especially the fibrous material comprises fibers having diameters selected from the range of 5-750 μm. Yet further, especially the fibrous material comprises fibers having lengths selected from the range of 50 μm-150 mm. Yet further, especially the fibrous material has a weight ratio of healing agent to (a) cement, and (b) one of more of slag, ash, limestone and sand selected from the range of 0.2:100-10:100. Yet further, especially the fibrous material has a weight ratio of fibrous reinforcing material to (a) cement, and (b) one of more of slag, ash, limestone and sand selected from the range of 0.1:100-10:100. The cementitious material, further may comprise water. The cementitious material may comprise a flowable mixture for a construction element, a paste, a mortar a plaster, etc. The cementitious material hence may require different flowabilities and different water to binder ratios. Especially the amount of water is related to the amount of binder, such as for instance cement, slag, ash, and limestone. In an embodiment the cementitious material may comprise cementitious material for high performance concrete. Especially such embodiment may comprise a low water-to-binder ratio. In an embodiment the ratio water-to-binder is 15:100. In another embodiment the ratio water-to-binder is larger than 40:100. In yet a further embodiment, the ratio is 60:100. Hence especially, the cementitious material may further comprise water, wherein the water-to-binder ratio selected from the range of 15:100-65:100. Especially the cementitious material is obtainable by the process described herein.

The phrase "the fibrous material has a weight ratio of healing agent to (a) cement, and (b) one of more of slag, ash, limestone and sand selected from the range of 0.2:100-10:100" indicates that the healing agent to the combination of materials of the first group (cement) and the second group (one of more of slag, ash, limestone and sand) has this ratio. Likewise, the phrase "the fibrous material has a weight ratio of fibrous reinforcing material to (a) cement, and (b) one of more of slag, ash, limestone and sand selected from the range of 0.1:100-10:100" indicates that the fibrous reinforcing material to the combination of materials of the first group (cement) and the second group (one of more of slag, ash, limestone and sand) has this ratio As indicated above, the invention provides a construction element comprising hardened cementitious material, wherein the cementitious material further comprises bacterial material and one or more of (i) fibrous reinforcing material comprising a biodegradable polymer, and (ii) a conversion product of a bacterial conversion of the fibrous reinforcing material comprises a biodegradable polymer. The construction element may e.g. be comprised by a building or a civil engineering structure, such as a department store, an office building, a bridge, a parking deck, a fly-over, a viaduct, a road, a dam, a dyke, a tunnel, a conduit. The construction element may also include a wall with bricks connected to each other via mortar. The construction element may also refer to the mortar only between bricks or other elements, i.e. the (hardened) mortar joint per se.

Hence, the invention also provides a method for the production of a construction element, the method comprising providing the cementitious material as defined in any one of the preceding claims, and allowing the cementitious material to harden at a predetermined place or in a predetermined mold. This method may include providing one or more building elements and joining these together with the cementitious material. In such embodiment, the cementitious material may be provided at the predetermined place on and/or at a side a first building element before arranging a second building element adjacent to the first building element, with the cementitious material in between the first building element and the second building element. Alternatively or additionally, two building elements may be arranged next to each other or on top of each other, and cementitious material may be provided in between the first building element and the second building element. In yet another embodiment, a mold may be provided to which the cementitious material may be provided (such as by depositing concrete). After hardening, the construction element is provided. Note that a larger structure, such as a house, a bridge, a department building, etc. may consist of a plurality of construction elements, but may also as a whole be considered as construction element. The mold can be a temporary mold, such as known in the art of construction. The construction element may optionally also be constructed (produced) under water.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. In the device claim enumerating several means, several of these means may be embodied by one and the same item of hardware. The mere fact that certain measures are recited in mutually different dependent claims does not indicate that a combination of these measures cannot be used to advantage.

The invention further pertains to a method or process comprising one or more of the characterising features described in the description and/or shown in the attached drawings. The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention further provides a kit of parts comprising the fibrous reinforcing material and the healing agent. For instance, a combination of two or more containers may be provided, one comprising the fibrous reinforcing material, and the other comprising healing agent. Optionally the kit of parts may be extended with cement starting materials (not including water). Hence, also a kit of parts may be provided comprising (i) one or more of the fibrous reinforcing material and the healing agent, optionally provided in separate containers, though optionally they may, when provided both, also be provided in a single container, and (ii) cement starting materials (not including water). The invention also provides a mixture comprising (i) one or more of the fibrous reinforcing material and (ii) the healing agent and cement starting materials (not including water). When all components are combined including water, again the cementitious material as described herein may be provided.

EXPERIMENTAL

Below, some fibers are indicated of which the first series are substantially not biodegradable (PE, PVA and PP), and the latter series (PBS, PHB and PLA) are biodegradable. Characteristic values are given:

| Fiber | | Tensile strength [MPa] | Elastic modulus [GPa] | Elongation at break [%] | Molecular weight [kg/mol] |
|---|---|---|---|---|---|
| Synthetic | | | | | |
| PE | Poly(ethylene) | 2700 | 120 | 3-80 | |
| PVA | Poly(vinyl-alcohol) | 1620 | 42.8 | 6 | |
| PP | Poly(propylene) | 770-880 | 11.2-13.2 | 17.6-25.7 | |

| Fiber | | Tensile strength [MPa] | Elastic modulus [GPa] | Elongation at break [%] | Molecular weight [kg/mol] |
|---|---|---|---|---|---|
| Bacterial | | | | | |
| PBS | Poly(butylene succinate) | 240-690 | 0.48-1.8 | 60-370 | 90 |
| PHB | Poly(hydroxy butyrate) | 190-740 | 3.8-7.7 | 24-60 | 530 |
| PLA | Poly(lactic acid) | 190-1200 | 3.88-15 | 39.2-73.6 | 100-3000 |

A cementitious mixture was made based on conventional cement starting materials. Bacterial material was added, and also PLA polymeric material and a calcium source. It was found that the mortar element (particulates ≤4 mm), made from the cementitious mixture had improved properties (especially liquid tightness) and the bacterial material use the degraded polymeric material, facilitating formation of crack filling calcium carbonate. Regain of liquid tightness was indicated by reduced water permeation in time by aqueous submersion of the cementitious element. Bacterial aerobic conversion of degraded polymer was indicated by oxygen consumption in an alkaline surrounding. Mineral deposition on degrading polymer and crack surfaces showed facilitation of calcium carbonate formation and crack blockage.

Further experiments were executed, providing evidence for microbial degradability of polymer fibres in alkaline environment. In an experimental test bacterial aerobic respiration (oxygen consumption) on polymer fibres suspended in alkaline solution (APS: artificial concrete pore solution, experimental model for concrete pore solution) was measured. The results are shown in the next table:

| Code | Containing | Bacterial respiration | Technical name |
|---|---|---|---|
| S16cont PVA/alg | polyvinyl alcohol/alginate-based fibre | ++ | N.A. |
| S15cont PVA/alg | polyvinyl alcohol/alginate-based fibre | ++ | N.A. |
| S14cont APIPLA | Polylactic acid | ++ | PLA1 |
| S13cont APIPLA | Polylactic acid | ++ | PLA2 |
| S7-Ingeo | Polylactic acid | + | Ingeo |
| S11-SC | Seaweed protein polymer | + | SeaCell |

Results show that bacterial oxygen respiration (oxygen consumption) on certain polymer fibres is high (relatively fast oxygen decrease in time), e.g. Fibre type S16cont PVA/alg (polyvinyl alcohol/alginate-based fibre comprising an alginate coated PVA back-bone), Fibre type S15cont PVA/alg (polyvinyl alcohol/alginate-based fibre), S14cont APIPLA (polylactic acid-based fibre), type S13 cont API-PLA (polylactic acid-based fibre). Results also show that bacterial oxygen respiration (oxygen consumption) on other types of polymer fibres is intermediate (slow oxygen decrease in time), e.g. Fibre S7-Ingeo, and S11-SC. These fibres basically are biodegradable. Apparently however they may are used to a lesser extend as a substrate for the bacterial material in the cementitious material.

It can thus be concluded from this experimental evidence that bacterial degradation (metabolic oxygen consumption) is high to moderate on specifically polyvinyl alcohol/alginate as well as polylactic acid—and seaweed protein based polymer fibres.

Yet further experiments were executed, providing evidence for functionality of microbial degradable polymer fibres as healing agent in cracked concrete specimens.

In an experimental test concrete specimens based on incorporated seaweed-derived protein polymer based fibres (SeaCell) were cracked, and subsequently submerged in bacteria-amended water suspension, after which mineral formation due to metabolic conversion of incorporated polymer fibres after 28 days incubation period was studied. Images were made of cracked concrete specimen, fortified with seaweed-derived protein polymer based fibres, image taken directly after cracking (first image), and after 28 days submersion in bacteria-amended water suspension (second image).

Likewise, an image (third image) was made of cracked concrete specimen, fortified with seaweed-derived protein polymer based fibres, image taken after 28 days submersion in water without added bacteria.

In a first image, with cracked concrete specimen, fortified with seaweed-derived protein polymer based fibres, image taken directly after cracking, crack-bridging polymer fibres were visible inside the crack. The second image showed the same cracked concrete specimen as depicted in image 1, after 28 days submersion in bacteria-containing water. Massive mineral deposits were visible both in the crack and on the surface of the concrete specimen, indicating that bacterial degradation of fibres results in mineral deposition. The third image, however, showed a cracked concrete specimen also containing seaweed-derived protein polymer fibres after 28 days submersion water to which no bacteria were added. Mineral deposits are insignificant in both the crack and on the surface of the concrete specimen, indicating that bacteria are required for degradation of fibres linked to mineral production.

It can thus be concluded from this experimental evidence that bacterial degradation of bacteria-degradable polymer fibres results in massive formation of mineral deposits, and that these mineral precipitates can contribute to concrete crack-healing (sealing) capacity. It can be furthermore concluded that absence of bacteria do not result in significant precipitation of minerals in cracked concrete specimens fortified with seaweed-derived protein polymer based fibres.

Below, examples of suitable base mixes for cementitious materials are provided. Here, some typical fibre lengths in cement-based (concrete) mixtures in relation concrete mix aggregate size are provided:

| | Mix ID | | | |
|---|---|---|---|---|
| | Mix1 | Mix2 | Mix3 | Mix4 |
| Cement (kg) | 233 | 442 | 526 | 516 |
| Blast-Furnice Slag (kg) | 543 | 132 | — | — |
| Fly ash (kg) | — | 563 | 631 | 620 |
| Limestone powder (kg) | 715 | — | — | 413 |
| Sand (kg) | — | 442 | 405 | — |
| Water (kg) | 416 | 361 | 365 | 384 |
| Superplastisicer* (kg) | 8.2 | 16.2 | 16.5 | 9.5 |
| Fibrous reinforcing material comprising a biodegradable polymer (kg) | 10 | 40 | 30 | 15 |
| Water-to-binder ratio | 0.27 | 0.33 | 0.33 | 0.25 |
| Maxium particle size (μm) | 150 | 500 | 500 | 200 |
| Fiber diameter (μm) | 39 | 39 | 39 | 39 |
| Fiber length (mm) | 8 | 8 | 8 | 8 |

*Cretoplast SL-01

These base mixes are further provided with the healing agent (comprising the bacteria and a building material (not shown in the table)). For instance, the healing agent may comprise organic compounds and/or bacteria-loaded porous particles. The healing agent may be added, wherein especially the amount of one or more of the binders (cement, blast-furnace slag, fly ash) and the sand are reduced. Best results have been obtained by adding a total of in the range of 0.2-10 kg healing agent to a mixture comprising 100 kg as the sum of cement, blast-furnace slag, fly ash, limestone powder and sand.

The maximum particle size (provided by sieving) in Mix 2 and 3 is 500 μm corresponding to the maximum particle size of the sand. In Mix 1, the maximum particle size is 150 μm, corresponding with the maximum particle size of the cement and the limestone powder. The maximum particle size in Mix 4 is 200 μm corresponding to the fly ash. Depending on the type of healing agent added to the mixture, the maximum particle size may however increase. Using porous particles having a maximum particle size of 1000 μm for instance increases the maximum particle size in the mixture also to 1000 μm.

The fibres of the fibrous reinforcing material, have a diameter of 39 μm and a length of 8 mm. Especially the aspect ratio (length/diameter) may be selected from the range of 30-250. The fibres were purpose-manufactured with a tensile strength (1620 MPa), elastic modulus (42.8 GPa), and a maximum elongation (6.0%) matching those needed for strain-hardening performance, and coated with a proprietary oiling agent 1.2% by mass. The fibre length over the aggregate size may be especially selected in the range of 1-100, more especially in the range of 2-10. The fibre volume may especially be selected from the range of 0.1-5% of the cementitious material.

Yet another example of a concrete mixture comprising natural Abaca fibers is given in the next table:

| Compound | Weight (kg) | Density (kg/m³) | Volume (dm³) |
| --- | --- | --- | --- |
| Gravel 4-8 mm | 564 | 2.7 | 209 |
| Expanded clay 1-4 mm | 130 | 0.85 | 153 |
| Sand 0.5-1 mm | 340 | 2.7 | 126 |
| Sand 0.25-0.5 mm | 361 | 2.7 | 134 |
| Sand 0.125-0.25 mm | 64 | 2.7 | 24 |
| Cement 42.5N | 392 | 3.15 | 124 |
| Water | 215 | 1 | 215 |
| Abaca fibres 20 mm | 5.6 | 1 | 5.6 |
| Total | 2066 | | 990 |

Again, a total of in the range of 0.2-10 kg healing agent may be added to such mixture comprising 100 kg as the sum of cement, blast-furnace slag, fly ash, limestone powder and sand.

The invention claimed is:

1. A process for the production of a cementitious material, comprising mixing cement starting materials, a healing agent and a fibrous reinforcing material, wherein the healing agent comprises bacterial material, wherein the fibrous reinforcing material comprises a biodegradable polymer, having an average molecular weight selected from the range of 10-1500 kg/mol, and wherein the fibrous material comprises fibers having diameters selected from the range of 5-750 μm, and having lengths selected from the range of 50 μm-150 mm.

2. The process according to claim 1, wherein the biodegradable polymer is selected from the group consisting of polybutylene succinate (PBS), polyhydroxybutyrate (PHB), and poly lactic acid (PLA).

3. The process according to claim 1, wherein the fibrous material comprises fibers having diameters selected from the range of 10-100 μm, and having lengths selected from the range of 0.5 mm-150 mm.

4. The process according to claim 1, wherein the fibrous material comprises fibers having lengths selected from the range of 50 μm-500 μm.

5. The process according to claim 1, wherein the bacterial material is selected from the group consisting of a bacterium, a lyophilized bacterium and a bacterial spore of a bacterium.

6. The process according to claim 5, wherein the bacterium is selected from the group consisting of aerobic bacteria.

7. The process according to claim 5, wherein the bacterium is selected from the group consisting of anaerobic bacteria.

8. The process according to claim 5, wherein the bacterium is selected from the group consisting of bacteria that can form a phosphate or a carbonate precipitate in an alkaline medium.

9. The process according to claim 5, wherein the bacterium is selected from the group of genera consisting of *Planococcus, Bacillus* and *Sporosarcina*.

10. The process according to claim 5, wherein the bacterium is selected from the group of denitrifying bacteria.

11. The process according to claim 1, wherein the healing agent comprises (1) one or more compounds selected from the group consisting of calcium formate, calcium acetate, calcium lactate, calcium gluconate, calcium nitrate, a carbohydrate, a fatty acid, a amino acid, a lactate, a maleate, a formate, a sugar, a pyruvate and a phytate and (2) a bacterial growth factor selected from the group consisting of a yeast extract, a peptone, an aspartate, a glutamate and trace elements.

12. The process according to claim 1, wherein the fibres are provided as textile of fibres.

13. A method for the production of a construction element, the method comprising providing the cementitious material as defined in claim 1, and allowing the cementitious material to harden at a predetermined place or in a predetermined mold.

14. A cementitious material obtainable by the process according to claim 1.

15. A cementitous material comprising (a) cement, (b) one of more of slag, ash, limestone and sand, (c) optionally super plastisizer, (d) healing agent, and (e) fibrous reinforcing material, wherein the healing agent comprises bacterial material, wherein the fibrous reinforcing material comprises a biodegradable polymer, having an average molecular weight selected from the range of 10-1500 kg/mol, and wherein the fibrous material comprises fibers having diameters selected from the range of 5-750 μm, and having lengths selected from the range of 50 μm-150 mm, having a weight ratio of healing agent to (a) cement, and (b) one of more of slag, ash, limestone and sand selected from the range of 0.2:100-10:100, and having a weight ratio of fibrous reinforcing material to (a) cement, and (b) one of more of slag, ash, limestone and sand selected from the range of 0.1:100-10:100.

16. The cementitious material according to claim 15, further comprising water, and having a water-to-binder ratio selected from the range of 15:100-65:100.

17. A construction element comprising hardened cementitious material, wherein the cementitious material further comprises bacterial material and one or more of (i) fibrous reinforcing material comprising a biodegradable polymer, and (ii) a conversion product of a bacterial conversion of the fibrous reinforcing material comprises a biodegradable polymer.

\* \* \* \* \*